United States Patent
Wellinghoff et al.

(10) Patent No.: US 6,417,244 B1
(45) Date of Patent: Jul. 9, 2002

(54) METAL OXIDE COMPOSITIONS AND METHODS

(75) Inventors: Stephen T. Wellinghoff, San Antonio; Hong Dixon, Helotes; Henry R. Rawls; Barry K. Norling, both of San Antonio, all of TX (US)

(73) Assignees: Southwest Research Institute, San Antonio; Board of Regents, The University of Texas System, Austin, both of TX (US)

(*) Notice: Subject to any disclaimer, the term of this patent is extended or adjusted under 35 U.S.C. 154(b) by 0 days.

(21) Appl. No.: 09/687,447

(22) Filed: Oct. 13, 2000

Related U.S. Application Data

(60) Continuation-in-part of application No. 08/721,742, filed on Sep. 27, 1996, now abandoned, which is a continuation-in-part of application No. 08/298,836, filed on Aug. 31, 1994, now Pat. No. 5,670,583, which is a division of application No. 08/047,750, filed on Apr. 13, 1993, now Pat. No. 5,372,796.

(51) Int. Cl.$^7$ .................................................. C08J 3/28
(52) U.S. Cl. ....................... 522/104; 526/116; 526/258; 526/260; 526/262; 526/263
(58) Field of Search .................. 522/104; 526/116, 526/277, 260, 258, 262, 263

(56) References Cited

U.S. PATENT DOCUMENTS

| | | | |
|---|---|---|---|
| 4,215,033 A | * | 7/1980 | Bowen |
| RE32,073 E | | 1/1986 | Randklev |
| 4,588,756 A | | 5/1986 | Bowen |
| 4,596,759 A | * | 6/1986 | Scupp ........................ 430/271 |
| 4,623,738 A | | 11/1986 | Sugerman et al. |
| 4,659,751 A | | 4/1987 | Bowen |
| 4,663,147 A | * | 5/1987 | DePrince ...................... 424/467 |
| 4,753,652 A | * | 6/1988 | Langer ........................... 623/1 |
| 4,842,987 A | * | 6/1989 | Elzer ........................... 430/281 |
| 4,964,911 A | | 10/1990 | Ibsen |
| 4,978,640 A | | 12/1990 | Kelly |
| 5,030,608 A | | 7/1991 | Schubert et al. |
| 5,057,018 A | | 10/1991 | Bowen |
| 5,064,877 A | * | 11/1991 | Nass ........................... 522/172 |
| 5,276,068 A | | 1/1994 | Waknine |
| 5,308,886 A | | 5/1994 | Masuhara et al. |
| 5,328,947 A | | 7/1994 | Taguchi et al. |
| 5,334,625 A | | 8/1994 | Ibsen et al. |
| 5,372,796 A | | 12/1994 | Wellinghoff |
| 5,472,797 A | | 12/1995 | Yajima et al. |
| 5,486,548 A | | 1/1996 | Podszun et al. |
| 5,502,087 A | | 3/1996 | Tateosian et al. |
| 5,556,931 A | | 9/1996 | Imura et al. |
| 5,663,214 A | | 9/1997 | Okada |
| 5,670,583 A | | 9/1997 | Wellinghoff |
| 5,730,601 A | | 3/1998 | Bowman et al. |
| 5,834,532 A | | 11/1998 | Yamamoto et al. |
| 5,852,248 A | | 12/1998 | Chadwick |
| 5,859,089 A | | 1/1999 | Qian |
| 5,865,623 A | | 2/1999 | Suh |
| 5,886,064 A | | 3/1999 | Rheinberger et al. |
| 5,897,885 A | | 4/1999 | Petticrew |
| 5,910,273 A | | 6/1999 | Thiel et al. |
| 5,955,514 A | | 9/1999 | Huang et al. |
| 5,998,499 A | | 12/1999 | Klee et al. |
| 6,027,816 A | | 2/2000 | Ono et al. |
| 6,031,015 A | | 2/2000 | Ritter et al. |

FOREIGN PATENT DOCUMENTS

| | | |
|---|---|---|
| CA | 2181507 | 7/1996 |
| EP | 0 159 877 A1 | 10/1985 |
| EP | 0159 877 A2 | 10/1985 |
| JP | H 3-344860 | 12/1991 |
| WO | WO 92/16183 | 10/1992 |
| WO | WO 94/24052 | 10/1994 |
| WO | WO 97/14674 | 4/1997 |
| WO | WO 98/13008 | 4/1998 |

OTHER PUBLICATIONS

Y. Wei, et al., "Synthesis of New Organic–Inorganic Hybrid Glasses"; Chem. Mater. 2(4), 337 (1990).
Steven T. Wellinghoff and Scott F. Timmons, Sol–Gel Processign and Application, Edited by Y.A. Attia, "Tantalum Oxide–Polymer Composites", Plemnum Press, New York, 1994, pp. 141–154.
H. Schmidt & H. Wolter, J. of Non. Cryst. Solids, 121. 428–435 (1990).
C.J.T. Landry, et al., Polymer, 33 (7). 1487 (1992).
M. Ellsworth et al. JACS, 113(7), 2756 (1991).
Michael J.S. Dewar, et al., "Factors Influencing the Stabilities of Nematic Liquid Crystals", Journal of American Chemical Society, (97), 23, 6658–6666.
Wolfgang Wedler, et al., "Vitrification in Low–molecular–weight mesogenic Compounds", J. Mater. Chem., 1991, 1(3), 347–356.
Sukmin Lee, et al., "Phase Behavior of Liquid Crystalline Polymer/Model Compound Mixtures: Theory and Equipment", Macromolecules, vol. 27, No. 14, 1994, 3955–3962.
R.A.M. Hikmet, et al., "Effect of the Orientation of the Ester Bonds on the Properties of Three Isomeric Liquid Crystal Diacrylates Before and After Polymerization", Macromolecules, vol. 28, No. 9, 1995, 3313–3327.

* cited by examiner

Primary Examiner—Fred Zitomer
(74) Attorney, Agent, or Firm—Paula D. Morris & Associates, P.C.

(57) ABSTRACT

Metal oxide and metal oxide-silica nanoparticles are disclosed wherein the surfaces thereof are complexed with a polymerizable, biocompatible, heterocyclic base. Polymerizable compositions are prepared by loading such nanoparticles into acrylate based monomer matrices, which compositions can then be photocured into X-ray opaque, transparent or translucent solids. Methods are disclosed for forming such complexed nanoparticles and compositions and for using such compositions as medical or dental restoratives.

30 Claims, No Drawings

METAL OXIDE COMPOSITIONS AND METHODS

CROSS REFERENCE TO RELATED APPLICATIONS

The instant application is a Continuation-in-Part of U.S. patent application Ser. No. 08/721,742, filed Sep. 27, 1996 abandoned, which is a Continuation-in-Part of U.S. application Ser. No. 08/298,836, filed Aug. 31, 1994 now U.S. Pat. No. 5,670,583 which is a Division of U.S. application Ser. No. 08/047,750, filed Apr. 3, 1993, now U.S. Pat. No. 5,372,796. The entirety of the specification and claims of the foregoing applications are specifically incorporated herein by reference.

BACKGROUND OF THE INVENTION

The instant invention relates to compositions primarily suitable for dental and medical restoration; i.e., dental filings or dental and bone adhesive, and to the method of their use for such purposes and methods of manufacture.

There have been repeated efforts to replace amalgam as a filling in dental practice, as well as to have suitable adhesives for dental purposes other than for fillings. One polymeric material that has been suggested for such use is bis-glycidlymethylmethacrylate polymer bis-GMA). When used as a dental adhesive or filling, together with the other usual components admixed therewith, such bis-GMA offers good mechanical and physical properties, but exhibits considerable post-shrinkage and relatively poor adhesion to bone substrate. Thus, it is not entirely satisfactory for use as an adhesive in dental work or as a filling. The use of such GMA material is disclosed in U.S. Pat Nos. 4,588,756 and 4,964,911.

Zero polymerization shrinkage is one of the most necessary features of a dental restorative so that accumulated stresses do not debond the dentin-restorative interface which can result in leakage and microbial attack.

U.S. Pat. No. 4,659,751 discusses the use of a variety of acids and other materials in order to treat the surface of teeth, such as enamel and dentin, to activate the surfaces for improved adhesion to polymers, but no disclosure or suggestion is made therein of the use of the GMA of bis-GMA.

In this regard, it is well known that in order to achieve desired bonding on enamel or dentin, the protein coatings on the enamel and the smear level on dentin must be removed. Traditionally, this has been done utilizing organic acids such as phosphoric, citric, and lactic acids, as well as ethylene diamine dicarboxylic acid. Accordingly, many of the new products provide such polyacids as surface cleaning and priming agents for enamel and dentin. At the present time bis-GMA resins themselves are not inherently adhesive to tooth surfaces, and if used acid etching is required.

Nematic liquid crystals are known which can be photopolymerized at high temperature, i.e., 90° C., within seconds with very low polymerization shrinkage to densely crosslinked networks of reaction extent greater than 95% by the usual free radical methods. The low polymerization shrinkage for such compounds originates from the high packing efficiency that already exists in the nematic state, thus minimizing the entropy reduction that occurs during polymerization.

However, polymerization at lower temperatures, such as room temperature, results in undesirable intervening smectic and crystalline phases making them unsuitable as photopolymerized medical and dental restoratives.

SUMMARY OF THE INVENTION

The foregoing problems and deficiencies of the prior art are overcome by the instant invention which provides especially low (essentially zero) polymerization shrinkage in the matrix resin while permitting high loading of strengthening materials and high matrix molecular weight, and yet permitting the matrix to strain soften, and flow onto and/or into areas to be cemented or restored, such as bone and tooth crevices, and be polymerized at room temperature.

Briefly, the present invention comprises novel transparent or translucent acrylate (or methacrylate) based matrix-metal oxide compositions, metal oxide nanoparticles with surface complexes, mixed particles formed by such nanoparticles with larger monosized silica particles to improve mechanical strength, and photopolymerizable room temperature nematics that have high strength and hardness with essentially zero shrinkage.

The invention also comprises the methods hereinafter set forth for making such tantalum oxide-silica microparticles, for making composites having reduced particle surface acidity, and the method of dental and bone restoration using the noted composites.

DETAILED DESCRIPTION

While the instant invention will be described with particular reference to use in the medical and dental fields, as in bone cements and dental restoratives, because of the high strength, hardness, substantially zero shrinkage, excellent adhesiveness and transparency or translucency of the composites, they can be used in other applications such as adhesives for woods, metals, and the like, or for forming resistant optical coatings and plaques.

While the present invention is carried out using any metal capable of forming amphoteric metal oxides to form the metal oxide nanoparticles, such as tantalum, niobium, indium, tin and the like it will be described in connection with tantalum. Tantalum is particularly desired for dental and medical uses since it will provide X-ray opaque materials necessary for subsequent review of the treated site; i.e., tooth or bone, by dentist and doctors.

These tantalum nanoparticles are prepared as set forth in the parent application identified above by ester exchange of tantalum oxide with an acid such as formic acid.

For this invention it is important that such nanoparticles be non-interacting without high surface acidity. High surface acidity is detrimental for dental applications. Accordingly, a polymerizable, biocompatible, heterocyclic base that can complex the acid sites on the surface of the tantalum oxide nanoparticles is admixed therewith. It is preferred to use alkene terminated imidiazoles and phosphates for this purpose with specific examples being 1-vinyl imidazole (VIM) and the phosphonated acrylic ester, PHEMA, formed by reacting diethylchlorophosphate with hydroxyethyl methacrylate (HEMA) in the presence of triethylamine in either. Such PHEMA has the formula:

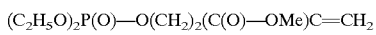

It will be evident that other like polymerizable imidazoles and phosphates can be utilized with, for example, compounds in which a liquid crystal moiety of the type set forth below is inserted between the alkene and imidazoles or alkene and phosphate moieties.

Such complexed tantalum oxide nanoparticles with imidazole or phosphate termination have no particle interaction or network formation and have enhanced coupling with the matrix resins(s).

As to the matrix monomers there are used photopolymerizable, acrylate based monomers, particularly those useful in dental applications. Particularly preferred are the bisacrylate terminated nematic liquid crystals having the formula:

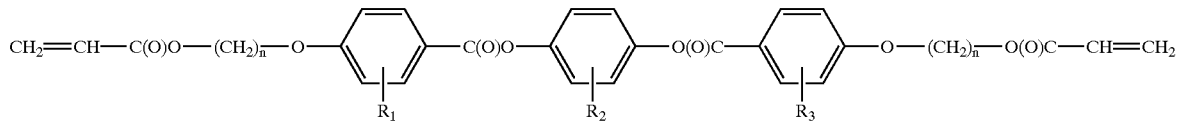

In this formula n is from 6 to 12, resulting in a $C_6$ to $C_{12}$ substituted or unsubstituted alkyl group, $R_1$ and $R_3$ are H or a methyl groups and $R_2$ is a bulky group adapted to provide sufficient steric hindrance to achieve a nematic state at room temperature while suppressing crystallinity of said liquid crystal monomers at room temperature. The large group size "mismatch" between the central aromatic group and the two surrounding aromatic groups is required to achieve these results.

The methacrylic derivatives of the above diacrylates are also suitable. Also, as discussed below, bis-GMA and other bis-glycidylacrylate and methacrylate compounds can be included in the matrix.

The method of making metal oxide clusters of the parent application permits growth of tantalum oxide particles of 1–2 nm in diameter. Assuming perfect boding between the particle and matrix, a decrease in particle size at a given volume fraction or particles will increase the elastic constraint on the deforming matrix molecules and leads to an increase in modulus. However, as the particle size approaches molecular dimensions, the very closely spaced crosslinking points of high functionality within the matrix will substantially quench any large scale molecular motions. It is these motions which are important for energy dissipation and fracture toughness.

Thus, for the purposes of this invention, particle sizes in the 50–100 nm sizes are more suitable. Also, the X-ray opacity of the composite material made from only tantalum oxide particles is too high for optimum diagnostic sensitivity. Therefore, in accord with the instant invention the Ta-nanoparticles are combined with relatively large, preformed silica particles has the advantage of increasing particle size and reducing X-ray opacity.

Monosized silica particles in the 10–20 nm diameter range are commercially available, but some are only stable as individual non-interacting particles at basic pH, where coagulation of the tantalum oxide nanoparticles will occur. Silica particles of 12 nm that are stable at acidic pH are available with a 13% aluminum oxide coating. These are supplied as concentrated water solutions that are stable at pH+4.5 and, in addition, are positively charged with chloride counterions. It has been found that when the naturally acidic methanol solutions of tantalum oxide nanoparticles are mixed with water solutions of this silica particle positive sol, clear stable solutions result which indicate excellent compatibility.

When the solvent is removed from this mixture, gelation occurs with subsequent insolubilization of the oxides. However, for Ta-oxide silica ratios>2, the addition of a strong complexing agent such as triethylphosphate or other organic phosphates permits complete solvent evaporation and subsequent dissolution into methanol. Substantial reduction or particle acidity is also observed when the surface protons on the tantalum oxide particles combine with chloride counterions of these silica particles and escape as HCl during vacuum evaporation. For weight ratios of Ta-oxide/ silica between 2 and 1, heterocoagulation takes place and then even the phosphate-complexed oxide is insoluble.

Organic phosphate triesters are known to be strong complexing agents for may metal ions with the potential to extract metal ions into hydrophobic phases. In order to take advantage of this complexing potential, the $Ta_2O_5$—$SiO_2$ composite is reacted with PHEMA. While PHEMA is a liquid at room temperature and is insoluble in water, it can be made soluble in water by the addition of a small quantity of methanol.

With this type of compound, the strategy is to utilize the diethylphosphate terminus to bind the nanoparticle surface and use the methacrylate end to copolymerize and couple the nanoparticles into the matrix resin.

In a typical procedure 40 wt. % of a 2:1 $Ta_2O$—$SiO_2$ composite with 60 wt % PHEMA was prepared by dissolving SiO particles and PHEMA in a methanol solution of Ta-oxide nanoparticles, and pumping the mixture dry at room temperature. The resultant gel was redissolved in methanol to form a clear mixture-indicating that the resulting nanoparticles were independent and non-associated, as intended. It was also found that bis-GMA can be partially substituted for PHEMA (up to 50 wt %) to make similar clear solutions.

The results of these studies establish the feasibility of using both imidazole and phosphate termination to attach reactive species to nano-particle surfaces so as to prevent particle interaction and network formation, and to enhance coupling to the matrix resin. They also demonstrate alternative routes to producing $Ta_2O/SiO_2$ composite particles with variable x-ray absorbance, in the optimum size range of 50–100 nm.

Dental practice requires that the matrix materials be fluids between room temperature and body temperature. Liquid crystalline diacrylates such as, bis(4-(10-acryloyloxylalyl- 1-oxy)benzoyll)2-(t-butyl)quinones and methacrylo derivatives are especially useful for this purpose. Although molecules of this structure have been synthesized, practical application in low polymerization shrinkage applications was precluded because of the development of crystallinity at room temperature which effectively prevents manipulation of the material. However, the novel substitution of the central aromatic group with an especially bulky group such as t-butyl was found to suppress crystallinity at room temperature while still permitting the nematic state to exist.

Thus, tests with bis-(4-(10-acryloyloxydecyl-loxy) benzoyl)2-t-butyl quinone, [C10(H,TB,H0] and bis-(4-(10-acryloyloxyhexyl-1-oxy)benzoyl)2-t-butyl quinone, [C6(H, TB,H)], were nematic in this temperature range and could be photopolymerized to strong solids with 1–2% polymerization shrinkage. However, substitutions, such as (C10(H,H,H), C10(H,MeO,H), C6(11,Me,H), C11(MeO,TB,MeO), C11MeO,H,Mc) and (MeO,Me,MeO) all resulted in materials with melting points above 50° C. (FIG. 2). As previously noted, achieving a nematic state at room temperature while suppressing crystallinity at the same temperature requires a large side group size mismatch between the central aromatic group and the two surrounding aromatic groups.

Even though liquid crystalline materials such as C10(H, H,H) melted above room temperature (ca85° C.) dilution of C10(H,H,H) WITH 50 WT % bisGMA generated a mobile liquid crystalline phase at room temperature (28° C.). This mobile liquid crystal phase converted to an isoptropic phase at 63° C.

It was possible to mix HEMA coated tantalum oxide nanoparticles prepared as above with this phase by co-dissolution of a HEMA solution of the C10(H,H,H) and bis-GMA and subsequent evaporation of the methanol. The mobile room temperature liquid crystal phase of 52 wt % Ta, 34%C10(H,H,H), 14% HEMA converted to an isotropic phase at 70° C.

While bis-GMA can be included as part of the matrix, other $C_1$ to $C_{12}$ acrylates and methacrylates can be used, such as bis-glycidylmethacrylate, bis-glycidylmethacrylate, bis-glycidylethylmethacrylate, 2-hydroxyethylmethacrylate; mixtures thereof, and the like.

The amount of nanoparticles added to the matrix can vary widely. Amounts of up to 40 wt % of nanoparticles for 100 wt. % of nanoparticles and matrix, can be utilized at amounts above about 40 wt %. The admixture becomes pasty. Obviously, the amount of lading is in the range necessary to give the desired final product and this can be determined for such particular nanoparticle and matrix used by routine experimentation.

In using the transparent or translucent nanoparticle-matrix composition, it need only be applied to the surface to be treated and photopolymerized. Thus, for use as a dental restorative, the liquid or pasty composition is placed on the tooth by a dentist or dental technician and ultra-violet light used to effect the polymerization (cure) into a high strength, hard, transparent, X-ray paque coating, or filling, with essentially zero shrinkage. Such essentially zero shrinkage is most important for fillings. Also, the transparency or translucency is an important characteristic, because it permits deeper photocure in thicker layers of the restorative composition, thus avoiding the multiple applications of opaque photocured restorative presently used.

While the invention has been described in connection with a preferred embodiment, it is not intended to limit the scope of the invention to the particular form set forth, but on the contrary, it is intended to cover such alternatives, modifications, and equivalents as may be included within th e spirit and scope of the invention as defined by the appended claims.

What is claimed is:

1. A composition photopolymerizable into transparent or translucent solids comprising:

a matrix comprising monomers selected from the group consisting of bisacrylate, bis-methacrylate, and a combination thereof;

particles comprising an amphoteric metal oxide, said particles selected from the group consisting of amphoteric metal oxide particles and amphoteric metal oxide-silica particles, said particles having a diameter in nanometers of about 50 to 100;

wherein said particles comprise a surface comprising acid sites complexed with or bound to a functionality selected from the group consisting of a phosphate group, a phosphonate group, and a heterocyclic basic atom of an alkene substituted polymerizable, biocompatible, monomeric, heterocyclic base.

2. The composition of claim 1 wherein said metal is tantalum and said base is selected from the group consisting of an alkene-terminated imidazole and an alkene-terminated phosphate.

3. The composition of claim 1 wherein said base is selected from the group consisting of 1-vinyl imidazole and $(C_2H_5O)_2P(O)=O(CH_2)_2(C(O)-O-Me)C=CH_2$.

4. The composition of claim 2 wherein said base is selected from the group consisting of 1-vinyl imidazole and $(C_2H_5O)_2P(O)=O(CH_2)_2(C(O)-O-Me)C=CH_2$.

5. The composition of claim 1 wherein said amphoteric metal oxide particles comprise tantalum oxide.

6. The composition of claim 2 wherein said amphoteric metal oxide particles comprise tantalum oxide.

7. The composition of claim 3 wherein said amphoteric metal oxide particles comprise tantalum oxide.

8. The composition of claim 4 wherein said amphoteric metal oxide particles comprise tantalum oxide.

9. A method of making photopolymerizable, transparent or translucent X-ray opaque compositions comprising admixing a matrix comprising monomers selected from the group consisting of bisacrylate monomers and bis-methacrylate monomers with X-ray opaque metal oxide particles comprising an amphoteric metal oxide, said particles having a diameter in nanometers of about 50 to 100, said metal oxide particles comprising a surface comprising acid sites complexed with or bound to a functionality selected from the group consisting of a phosphate group, a phosphonate group, and the heterocyclic basic atom of an alkene substituted polymerizable, biocompatible, monomeric, heterocyclic base.

10. The method of claim 9 wherein said metal is tantalum and said base is selected from the group consisting of an alkene-terminated imidazole and an alkene-terminated phosphate.

11. The method of claim 9 wherein said base is selected from the group consisting of 1-vinyl imidazole or $(C_2H_5O)_2P(O)=O(CH_2)_2(C(O)-O-Me)C=CH_2$.

12. The method of claim 9 wherein said amphoteric metal oxide comprises tantalum oxide.

13. The method of claim 10 wherein said amphoteric metal oxide comprises tantalum oxide.

14. The method of claim 11 wherein said amphoteric metal oxide comprises tantalum oxide.

15. A composition photopolymerizable into transparent or translucent solids comprising:

a matrix comprising monomers having the following general structure:

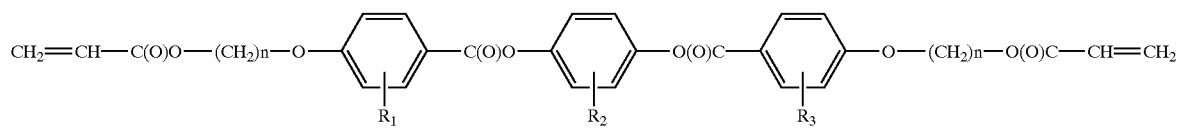

wherein n is from about 6 to about 12;

R1 and R3 are selected from the group consisting of hydrogen and a methyl group; and R2 is an organic group having greater bulk than R1 and R3, wherein said bulk is sufficient upon polymerization to produce a transparent or translucent solid which consists essentially of a nematic state at room temperature; and particles comprising an amphoteric metal oxide, said particles selected from the group consisting of amphoteric metal oxide particles and amphoteric metal oxide-silica particles, said particles having a diameter in nanometers of about 50 to 100;

wherein said particles comprise a surface comprising acid sites complexed with an alkene terminated polymerizable, biocompatible, monomeric, heterocyclic base.

16. The composition of claim 15 wherein said metal is tantalum and said base is selected from the group consisting of an alkene-terminated imidazole and an alkene-terminated phosphate.

17. The composition of claim 15 wherein said base is 1-vinyl imidazole or $(C_2H_5O)_2P(O)=O(CH_2)_2(C(O)-O-Me)C=CH_2$.

18. The composition of claim 15 wherein said amphoteric metal oxide particles comprise tantalum oxide.

19. The composition of claim 16 wherein said amphoteric metal oxide particles comprise tantalum oxide.

20. The composition of claim 17 wherein said amphoteric metal oxide particles comprise tantalum oxide.

21. The composition of claim 15 wherein said matrix comprises a mixture of said monomers.

22. The composition of claim 16 wherein said matrix comprises a mixture of said monomers.

23. The composition of claim 17 wherein said matrix comprises a mixture of said monomers.

24. The composition of claim 18 wherein said matrix comprises a mixture of said monomers.

25. The composition of claim 19 wherein said matrix comprises a mixture of said monomers.

26. The composition of claim 20 wherein said matrix comprises a mixture of said monomers.

27. A method of dental repair comprising applying to a dentin surface the photopolymerizable composition of claim 1.

28. A method of dental repair comprising applying to a dentin surface the photopolymerizable composition of claim 8.

29. A method of dental repair comprising applying to a dentin surface the photopolymerizable composition of claim 21.

30. A method of dental repair comprising applying to a dentin surface the photopolymerizable composition of claim 26.

* * * * *

UNITED STATES PATENT AND TRADEMARK OFFICE
CERTIFICATE OF CORRECTION

PATENT NO.   : 6,417,244 B1
DATED        : July 9, 2002
INVENTOR(S)  : Wellinghoff et al.

It is certified that error appears in the above-identified patent and that said Letters Patent is hereby corrected as shown below:

Column 1,
Line 16, after the reference to prior applications, please insert as a second paragraph -- The U.S. government has certain rights in this invention pursuant to grant number NIDCR 1 PO1 DE11688. --

Signed and Sealed this

Eleventh Day of February, 2003

JAMES E. ROGAN
*Director of the United States Patent and Trademark Office*